(12) United States Patent  (10) Patent No.: US 7,588,035 B2
Ponzini  (45) Date of Patent: Sep. 15, 2009

(54) FLOSS BOW AND DISPOSABLE FLOSS CARTRIDGE THEREFOR

(75) Inventor: Eligio Ponzini, Milan (IT)

(73) Assignee: Ponzini S.p.A., Lazzate, Milan (IT)

( * ) Notice: Subject to any disclaimer, the term of this patent is extended or adjusted under 35 U.S.C. 154(b) by 0 days.

(21) Appl. No.: 11/485,253

(22) Filed: Jul. 13, 2006

(65) Prior Publication Data

US 2007/0012332 A1 Jan. 18, 2007

(30) Foreign Application Priority Data

Jul. 14, 2005 (IT) .................. MI2005A001343

(51) Int. Cl.
*A61C 15/00* (2006.01)
(52) U.S. Cl. .................................... 132/321
(58) Field of Classification Search .......... 132/321–329
See application file for complete search history.

(56) References Cited

U.S. PATENT DOCUMENTS

| | | | | | |
|---|---|---|---|---|---|
| 1,091,789 | A | * | 3/1914 | Andren | 132/323 |
| 3,236,247 | A | * | 2/1966 | Brockman | 132/323 |
| 3,387,615 | A | * | 6/1968 | Mackew | 132/323 |
| 3,759,272 | A | * | 9/1973 | Di Vincenti | 132/326 |
| 3,828,804 | A | * | 8/1974 | Ely | 132/323 |
| 3,910,294 | A | * | 10/1975 | Reed | 132/323 |
| 3,987,806 | A | * | 10/1976 | Gilbert | 132/323 |
| 3,998,236 | A | * | 12/1976 | Koo | 132/324 |
| D275,039 | S | * | 8/1984 | Loubier | D28/68 |
| 4,550,741 | A | * | 11/1985 | Krag | 132/321 |
| 4,727,895 | A | * | 3/1988 | Berarducci | 132/323 |
| 5,086,792 | A | * | 2/1992 | Chodorow | 132/323 |
| 5,183,064 | A | * | 2/1993 | Barth | 132/323 |
| 5,931,171 | A | * | 8/1999 | Landis et al. | 132/323 |
| 6,155,274 | A | * | 12/2000 | Stein | 132/327 |
| 2003/0226575 | A1 | * | 12/2003 | Lee | 132/327 |

FOREIGN PATENT DOCUMENTS

| | | |
|---|---|---|
| DE | 86 05 684 | 4/1986 |
| EP | 0 904 744 | 3/1999 |
| GB | 778564 | 7/1957 |

* cited by examiner

*Primary Examiner*—Robyn Doan
(74) *Attorney, Agent, or Firm*—Young & Thompson

(57) ABSTRACT

A floss bow includes a main body from which at least a pair of tines projects. A floss may be tightened around the tines. The main body also includes a retaining column. The floss is a member of a disposable, replaceable cartridge, which has a rigid portion which may be removably fastened to the retaining column.

7 Claims, 2 Drawing Sheets

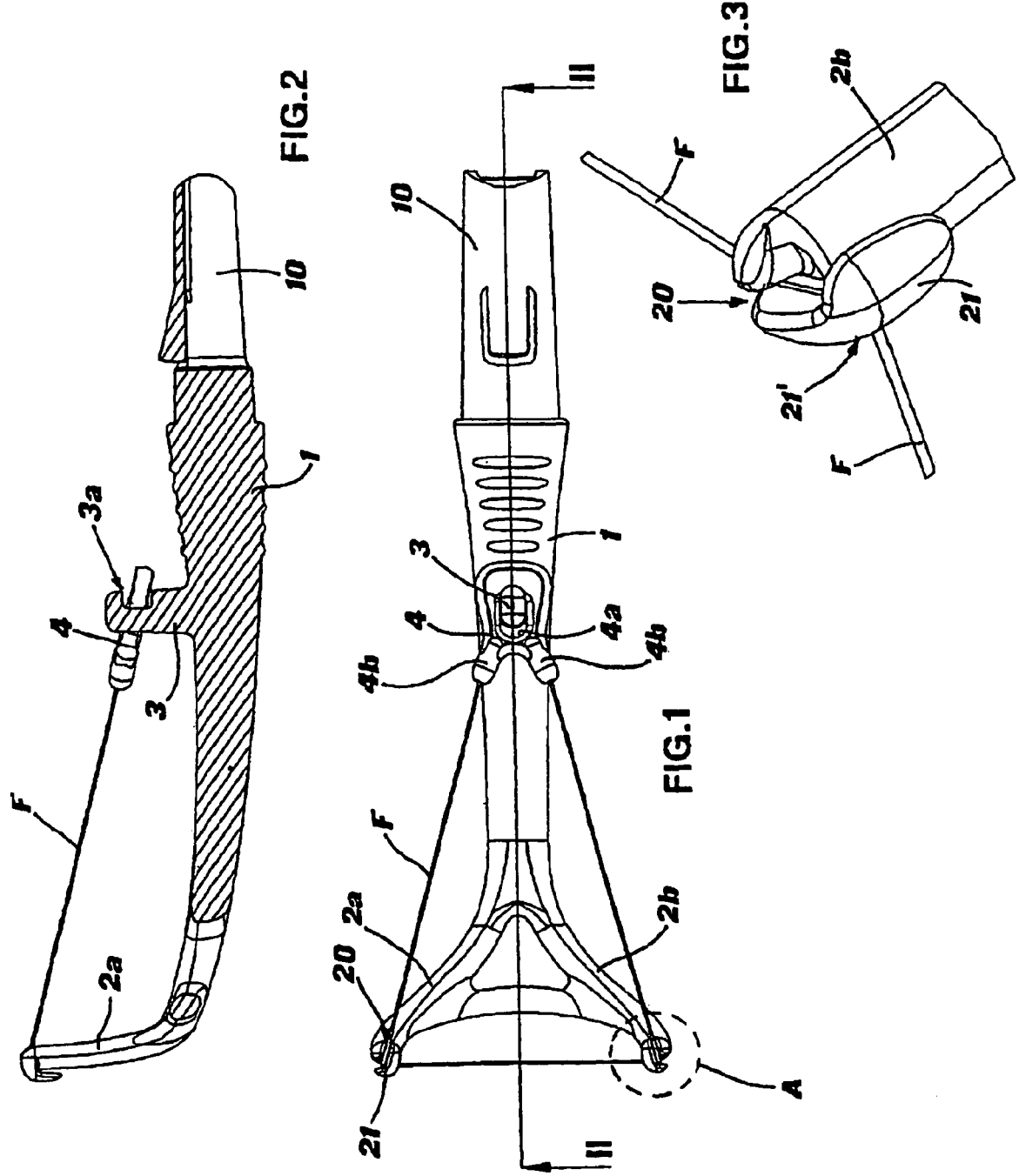

FLOSS BOW AND DISPOSABLE FLOSS CARTRIDGE THEREFOR

BACKGROUND OF THE INVENTION

The present invention concerns a floss bow, in particular a bow employing replaceable floss.

As known, floss is available to the end user substantially in two formats: one as a spool of floss in small dispensing boxes, the other as a length of floss kept taut on a supporting fork or bow. The present invention refers to this last sector, which will therefore be the subject of the following description.

According to the prior art, sections of floss are tightened and fastened to the ends of a pair of tines belonging to a bow or fork device, typically made of cheap plastics. The bow may be of a minimal size, but it sometimes appears awkward to handle, or it may also comprise a more substantial handle to be gripped by a hand.

Since a short length of floss may be employed few times, these bows are generally designed to be inexpensive because they are then disposed of together with the floss. Where they have a handle, it has already been suggested to make the bow portion disengageable from the handle portion (for example the Reach® Access™ system manufactured by Johnson & Johnson), so as to reduce the amount of plastics disposed of every time.

However, the plastic portion which is disposed of together with the floss is nevertheless considerable, since it comprises at least the two support tines with the common strengthening body.

In order to partly overcome this problem it has been suggested to apply spools of floss on a handle provided with an end bow: thereby the floss is tightened between the bow tines and replaced, as it is being used, with the floss stored in the spool. An example found on the market is Flosbrush® manufactured for John O. Butler Company.

In this case no plastic components are disposed of, but handling of the floss is very awkward and fastening of the floss to the tine ends is neither intuitive nor easy for everybody.

Moreover, in all the bows available so far, the problem still exists of best defining the distance between the support tines and hence the length of the useful floss segment. As a matter of fact, such length is always a compromise between a minimum size—which, however, implies quick floss consumption and poor mobility between teeth—and a maximum dimension, determined by the need to easily introduce the tool in the mouth.

Again, the arrangement and orientation of the useful length of floss over the gripping portion or the handle are univocally determined, although they are not ideal to clean every part of the dental arch: here, too, it is hence still necessary to operate a compromise choice.

SUMMARY OF THE INVENTION

The object of the present invention is hence to solve the above-mentioned problems, in particular by providing a bow suitable to host an easily replaceable length of floss, with a minimum disposal of plastic material, of a suitable length to ensure effectiveness and durability, as well as positioned and directed in a way suitable to the various parts of the mouth.

Namely, according to a first aspect of the invention, a floss bow is provided, of the type comprising a main body wherefrom at least one pair of tines projects, around which a piece of floss may be tightened, wherein said main body further comprises a retaining column and said floss is part of a disposable, replaceable cartridge which further comprises a rigid portion which may be removably fastened to said retaining column.

According to a second aspect of the invention, said replaceable cartridge extends over a smaller linear development than the linear development existing between said retaining column and the ends of said tines, so that mounting of the cartridge on the bow causes an elastic deflection of the tines and/or elastic stretching of the floss.

According to a third aspect of the invention said rigid portion of the cartridge is shaped as a plate integral with a length of said floss arranged in a loop and configured so as to be capable of being engaged with said retaining column. Preferably, said plate has an eyelet which may be introduced in a hook-type head of said column.

According to a further aspect, the end of each of said tines has a groove wherein said floss may be introduced; preferably, a side portion defining said end groove extends into a slip-proof flap which runs downwards to the tine root parallel to the tine front side.

Finally, according to another aspect of the invention, the tines and the retaining column project from the main body of the bow in a direction perpendicular to the main axis of a handle thereof. Possible, said tines are arranged in an asymmetrical position with respect to the longitudinal axis of the main body.

BRIEF DESCRIPTION OF THE DRAWINGS

Further features and advantages of the device according to the invention will in any case be more evident from the following detailed description of a preferred embodiment of the same, given by way of example and illustrated in the accompanying drawings, wherein:

FIG. 1 is a top plan view of a preferred embodiment of the invention;

FIG. 2 is a cross-section view along line II-II of FIG. 1;

FIG. 3 is a perspective enlarged view of the encircled detail A of FIG. 1;

DETAILED DESCRIPTION OF THE PREFERRED EMBODIMENTS

Figure 5:
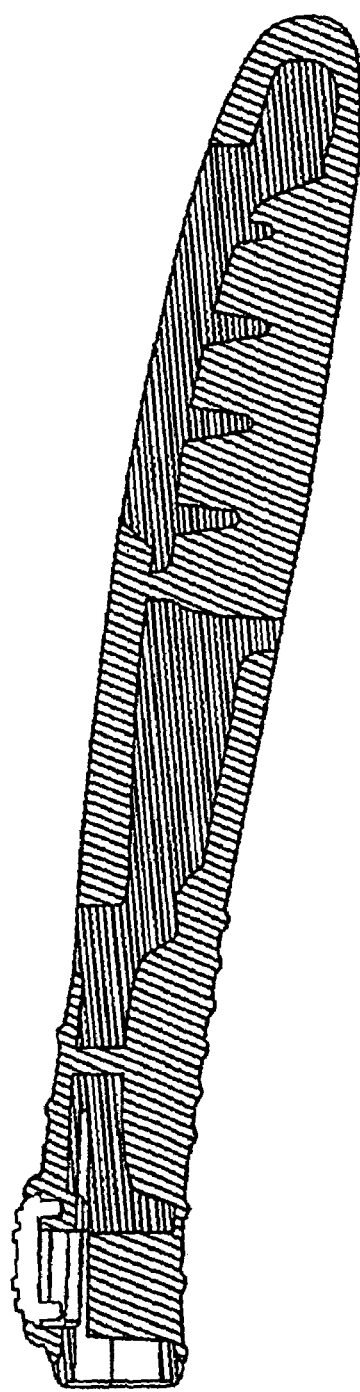
FIG. 5 is a cross-section view along line V-V of FIG. 4.
Figure 4:
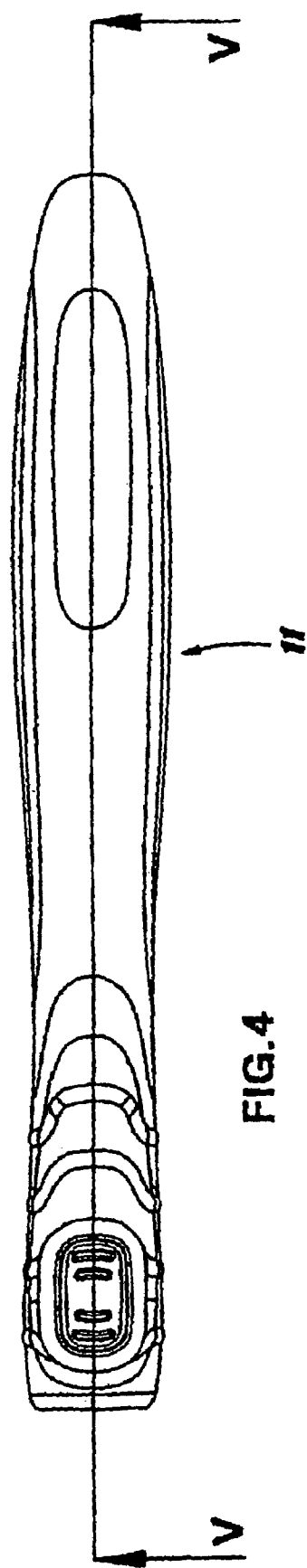
FIG. 4 is a top plan view of a handle to be used with the device of FIG. 1.

A floss bow has, in a manner known per se, a main body 1 from the front end of which a pair of tines 2a and 2b departs, such tines ending spaced apart at a certain mutual distance, for example 24 mm.

According to the invention, from main body 1 a retaining column 3 with a hook-shaped end head 3a also departs.

Moreover, the ends of tines 2a and 2b are provided with at least one groove capable of introducing a floss therein.

The device is completed by a replaceable floss cartridge comprised of a looped length of floss F, retained on a small drilled plate 4 of a more rigid material, for example moulded in polypropylene. As can be appreciated in FIG. 1, drilled plate 4 is substantially flat and is sized so as to be capable of being gripped by the fingers of a hand. It is provided with an eyelet 4a into which the hook-shaped head of column 3 may be introduced.

Preferably, from plate 4 two short arms 4b project by a short length, which are directed, when the cartridge is in its operating position, engaged with the head 3a of column 3, towards the ends of the two tines 2a and 2b.

The two arms 4b incorporate and guide the converging ends of floss F, according to an angle which defines the vertex of an ideal triangle according to which the floss sets itself in its operating position.

Depending on the floss material, retaining of the floss on plate 4 may be simply achieved by overmoulding or—as in the case of a floss which may not be bonded to the plate material—by previously providing end enlargements on the floss/thread, for example small knots. Moreover, in the future floss technology may make a continuous floss loop available: in such case the floss would of course be retained simply by overmoulding plate 4 in any floss position.

For cartridge assembly on bow body 1, it is sufficient to engage floss F with the grooves at the ends of tines 2a and 2b, and to then pull back plate 4, pinching the same between one's fingers, until the floss is taut and eyelet 4a may be inserted over head 3a of column 3. The length of floss, as well as the relative distance between column 3 and tines 2, are provided in such a way that in this engagement step an elastic deformation of tines 2 and/or of the floss is obtained: the resulting floss tension, due to a natural bias of these components towards their unstressed status, ensures that the engagement of eyelet 4a with the hook-shaped head 3a of column 3 is stable and is maintained in all conditions of use, as long as one acts willingly on plate 4 again to slide it off head 3a. Moreover, this device arranges the floss in an ideal condition for use.

It can be appreciated that, due to the cartridge being arranged on the ends of the tines and on the hook-shaped head of column 3, the entire floss remains well raised with respect to the main body 1 of the bow, hence being active on the entire length for use in the gaps of the dental arch. As a result, the floss may easily be used on all three sides of the triangular pattern defined by the floss cartridge.

In the advantageous embodiment shown, bow body 1 is further provided with an engagement extension 10, by which it may temporarily be coupled with a handle portion 11 (FIGS. 5 and 6). The engagement system, however, will not be shown in further detail here, as it is the subject matter of another application concurrently filed by the same Applicant.

According to a preferred embodiment, the end of tines 2a, 2b does not exhibit a simple groove into which said floss may be introduced and retained, but also a slip-proof flap 21.

The slip-proof flap 21 extends from a groove side and runs down from the top of each tine 2a and 2b, extending by a short distance parallel to the tine on its front side, as is clearly visible in FIG. 3. During assembly of the floss cartridge onto body 1, the presence of flap 21 forces one to insert floss F between flap 21 and its respective tine, causing said floss to translate from the tine root to the tine top. Once floss F is set against base 21' of the flap, floss F may be caused to deviate or flex to cross over the tine top end, and is introduced into groove 20, then tensioned and retained on column 3 through plate 4. Despite this greater complexity of mounting, it is ensured that the floss cannot accidentally come out of groove 20, being retained by base 21' of flap 21. This solution is particularly advantageous as it prevents the floss from coming off the bow even if, during use between dental gaps, a tensile strength tending to remove the floss from grooves 20 is imparted.

It can further be noted that the specific configuration of the flap 21 shown in FIG. 3 nevertheless allows to mould the bow and its corresponding tine with a single mould-countermould pair, without having to perform complex removal operations of the moulding components.

As can be understood, the objects set forth in the preliminary remarks are perfectly achieved through the bow according to the invention.

As a matter of fact, the floss cartridge, though being shorter than a spool, is nevertheless of a significant size, so as to avoid early run-out, since the floss runs on three useful sides. Moreover, the triangle-like arrangement allows to exploit three different floss orientations with respect to the handle, which aids an effective and advantageous use in many parts of the dental arch. Again, the replaceable cartridge element has a very small plastic portion, coinciding with plate 4, with a consequent negligible economic and environmental impact.

It is intended, however, that the invention is not limited to the specific embodiments illustrated above, which represent only non-limiting examples of the scope of the invention, but that a number of variants are possible, all within the reach of a person skilled in the field, without departing from the scope of the invention.

For example, although a bow having its two tines arranged symmetrically with respect to a longitudinal axis has been described, the arrangement can be provided to also be asymmetrical and hence, once the replaceable cartridge has been mounted, the floss arranges itself according not to an isosceles triangle shape, but to a triangle shape more suited to the user's needs. Advantageously, in the embodiment having a handle which may be coupled with the bow, such as the illustrated one, it is possible to supply the consumer with a set of different bows, which he will use as he sees fit even with the same floss cartridges.

The invention claimed is:

1. A floss bow in combination with a disposable, replaceable floss cartridge, comprising:
    a floss bow main body having a handle;
    at least one pair of tines projecting from said main body;
    a retaining column having a head projecting from said main body, said tines and said retaining column projecting from said main body on a same side of said main body in a direction perpendicular to a main axis of said handle of said main body, said tines being elastically deformable; and
    a disposable, replaceable floss cartridge including floss, said cartridge comprises a rigid portion which is removably fastenable to said retaining column, the cartridge extending over a smaller linear distance than a linear distance defined between said retaining column and ends of said at least one pair of tines, so that mounting of the cartridge on the bow causes an elastic deflection of the at least one pair of tines, said floss forming a triangle in its operating position, a base of said triangle being substantially coplanar with sides of said triangle, said rigid portion having an eyelet which is introducable in said head of said column.

2. The combination as in claim 1, wherein said rigid portion of the cartridge is shaped as a plate integral with a length of said floss arranged in a loop and configured so as to be engagable with said retaining column.

3. The combination as in claim 1, wherein the end of each of said at least one pair of tines has a groove for introducing said floss.

4. The combination as in claim 3, further comprising a slip-proof flap on each tine which runs downwards to a base of the tine parallel to a front side of the tine.

5. The combination as in claim 3, wherein said groove extends towards said column.

6. The combination as in claim 1, wherein said at least one pair of tines are arranged in an asymmetrical position with respect to the longitudinal axis of the main body.

7. A floss bow, comprising:

a main body having a handle extending substantially in a longitudinal direction;

a pair of tines divergently extending from one end of said main body, said tines curving away from said main body so as to project in a direction substantially perpendicular to a main axis of said main body, said tines being structured and arranged so that a piece of floss is tightenable around respective distal ends thereof; and a retaining column projecting from said main body in a direction substantially perpendicular to said main axis of said main body in a same direction as said tines, said retaining column having a hook-shaped portion extending in said longitudinal direction away from said tines, wherein the distal end of each of said pair of tines has a groove for introducing said floss, said groove extending along a topmost portion of said tines substantially in said longitudinal direction, wherein said piece of floss is part of a disposable, replaceable cartridge which comprises a plate integral with a length of floss arranged in a loop, said plate having an eyelet, and has two arms that project from a body of said plate, a respective end of said floss being connected to a corresponding one of said two arms so that the floss converges together at said plate.

* * * * *